(12) United States Patent
Kania

(10) Patent No.: US 6,228,021 B1
(45) Date of Patent: *May 8, 2001

(54) APPARATUS AND METHOD FOR RELIEVING MOTION SICKNESS

(75) Inventor: Bruce Kania, Bozeman, MT (US)

(73) Assignee: Fountainhead, Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/263,777

(22) Filed: Mar. 5, 1999

(51) Int. Cl.[7] .............. A61M 21/00; H03G 5/00; H04R 5/02
(52) U.S. Cl. .............. 600/27; 128/898; 128/897; 381/98; 381/309
(58) Field of Search .............. 600/27; 128/897, 128/898; 702/150; 381/98, 103

(56) References Cited

U.S. PATENT DOCUMENTS

| | | |
|---|---|---|
| 4,016,535 | 4/1977 | Dinlocker . |
| 4,267,547 | 5/1981 | Sugiyama . |
| 4,408,196 | 10/1983 | Freeman . |
| 4,528,559 | 7/1985 | Freeman . |
| 4,647,928 | 3/1987 | Casey et al. . |
| 4,697,174 | 9/1987 | Viator, Sr. . |
| 4,930,435 | * 6/1990 | Newman .............. 114/191 |
| 5,033,694 | 7/1991 | Sato . |
| 5,161,192 | * 11/1992 | Ferguson .............. 381/1 |
| 5,161,196 | 11/1992 | Ferguson . |
| 5,367,297 | 11/1994 | Yokoyama . |
| 5,791,982 | 8/1998 | Curry et al. . |
| 5,966,680 | * 10/1999 | Butnaru .............. 702/150 |
| 6,042,533 | * 3/2000 | Kania .............. 600/27 |

* cited by examiner

Primary Examiner—Forester W. Isen
Assistant Examiner—Brian Tyrone Pendleton
(74) Attorney, Agent, or Firm—Oblon, Spivak, McClelland, Maier & Neustadt, P.C.

(57) ABSTRACT

A method and apparatus used for relieving motion sickness, wherein a sensor senses a motion of an object and a sensory converter coupled to the sensor and converts the sensed motion to corresponding sensory signals for presentation to a user. The sensory signals include audio signals, display signals, white noise signals, pink noise signals, brown noise signals, and audio tone signals The audio signals, white noise signals, pink noise signals, and brown noise sensory signals have a variation in spectral emphasis in proportion to the sensed motion, such as by varying a bandwidth, a center frequency, and an amplitude of a first range of the sensory signals. The display signals have a variation in a display characteristic and the audio tone signals have a variation in time intervals between successive audio tones. The audio tones may also include audio messages containing words. The sensory signals are used to resolve a conflict between vestibular, ocular, and proprioceptive inputs of the user, thus relieving motion sickness.

30 Claims, 8 Drawing Sheets

APPARATUS AND METHOD FOR RELIEVING MOTION SICKNESS

CROSS-REFERENCE

This application is related to co-pending application Ser. No. 09/121,720, filed on Jul. 24, 1998, which is incorporated in its entirety.

BACKGROUND OF THE INVENTION

1. Field of the Invention

The present invention relates to a method and apparatus for relieving motion sickness. More particularly, the present invention is related to providing individual sensory signals that correspond to the motion of a craft, or in another aspect, proximity of potential obstacles, so that the individual may use these signals to improve a sense of equilibrium or to avoid collision with the obstacles.

2. Discussion of the Background

Essentially, motion sickness occurs as a result of an unusual motion experience. When a person is unable to predict or anticipate this unusual motion, the person's equilibrium may be effected. The phenomenon of motion sickness may be derived from a principle researched by Dr. David Winters, a retired University of Waterloo professor, and which is referred to as "The Principle of Indeterminacy."

The principle of indeterminacy describes a human's natural ability to identify changes in the neuromuscular skeletal system and to adapt to a new optimum motion. For example, if a prosthetic leg does not offer comparable function, an amputee will favor the remaining leg. Thus, the residual limb becomes weaker and the remaining leg becomes stronger. The option to utilize the prosthesis or the natural leg represents a conflict, i.e., between walking in a conventional symmetrical manner or favoring the natural leg. The person, without conscious volition, chooses favoring the natural side when the choice is perceived by the human's body as optimal. Currently, it is not known for certain which senses are most influential in making this choice. However, it is likely that pain and comfort, proprioceptive, vestibular, and ocular inputs affect this choice.

Similarly, motion sickness results from a conflict between these vestibular, ocular and proprioceptive inputs. For example, conventional wisdom among charter boat operators is that charter boat captains do not get seasick, unless they spend a significant amount of time below deck, whereas captains of cruise ships are known to be somewhat more susceptible to motion sickness. This is because a charter boat captain usually sits high in the cabin, a position from where he can observe quite clearly what the relatively small charter boat is about to experience. Thus, he has accurate visual data which reconciles a conflict between the vestibular, ocular, and proprioceptive inputs. On the contrary, the captain of a large cruise ship cannot see what is taking place immediately in front of the ship's bow. Thus, a conflict between the vestibular, ocular, and proprioceptive data is not resolved.

Motion sickness is very costly for many industries. For example, the airline industry loses millions of dollars per year from passengers who are unwilling to travel because they experience motion sickness. The same can be said for cruise ships. In addition, if a person experiences motion sickness while operating a dangerous vehicle, injury or even a loss of life may occur.

Thus, a need for a device which relieves or prevents motion sickness will have a significant impact on society. One proposed motion sickness device is that described in Ferguson (U.S. Pat. No. 5,161,196). Ferguson discloses positioning an array of sound emitters at the sides of an enclosure and varying the sound levels from selected emitters in response to changes in the enclosure's movement. To an individual, the sound source is not perceived as rolling with the vehicle but rather is inertially stable while the vehicle rolls relative to the sound source. That is, Ferguson is directed to creating an artificial sound horizon which is acoustically perceivable to the individual and continuously maintaining the sound horizon substantially positionally stationary with reference to a fixed horizon of the enclosure.

However, one problem with Ferguson is that an artificial sound horizon is created. This artificial sound horizon (i.e., between sound emitters at opposite sides of the enclosure) may cause an individual to experience further motion sickness because a conflict is created between the vestibular, ocular, and proprioceptive inputs and the artificial sound horizon. Further, another problem with Ferguson is that an array of sound emitters (e.g., speakers) placed at specific locations chosen in accordance with a predicted motion of the enclosure are required. That is, the speakers are required to be located in opposite sides of the enclosure.

SUMMARY OF THE INVENTION

Accordingly, an object of the present invention is to provide a novel apparatus and method for relieving motion sickness.

Another object of the present invention is to relieve motion sickness by presenting a user with at least one sensory signal including an audio signal, a white noise signal, a pink noise signal, a brown noise signal, a popcorn noise signal, or combinations thereof which have a variation in spectral emphasis in proportion to a sensed motion of an object, so that the user may resolve a conflict between vestibular, ocular, and proprioceptive inputs. The variation in spectral emphasis includes, for example, a variation in a bandwidth, a center frequency, and an amplitude of a first range of the sensory signals. Further, the sensory signals may also include display signals presented on a display. The display signals may be presented on the display as display elements having, for example, a shape, a size, an intensity, and a color. For example, the display elements may include a blue square, red circle, green star, etc. In addition, the display elements may have a variation in a display characteristic, such as a variation in a size, a shape, an intensity, and a color of the display elements. The variation in display characteristic is based on the sensed motion of the object. In addition, the sensory signals may include audio tone signals which have a variation in time intervals between successive tone signals. The variation in time intervals is based on the sensed motion of the object.

Yet another object of the present invention is to provide a device for assisting an individual which suffers from a severe vestibular imbalance by presenting this individual with audio, white noise, pink noise, brown noise or audio tone sensory signals corresponding to a sensed motion of the individual. White noise is a random noise containing all frequencies and sounds similar to the "hiss" noise generated by an FM radio receiver when tuned off station. That is, white noise is a random noise that has a flat frequency spectrum at the frequency range of interest. In addition, pink, brown or popcorn noise signals may also be used. Pink noise is a random noise whose spectrum level has a negative slope of 10 decibels per decade (i.e., any noise with a power spectrum that falls as a power spectrum of 1/f), and brown noise has a power spectrum of 1/f. The name "brown noise"

comes from Brownian motion, which is the random motion of small objects in fluids. Ordinary music tends to have a brown power spectrum, whereas white noise tends to sound noisy or busy, and pink noise sounds overly simple. Popcorn noise includes individual events whose magnitude distribution does not have a maximum at zero and is not even symmetric about zero. Popcorn noise includes isolated spikes in the output voltage and the voltage height of spikes has a mean value that is significantly (i.e., by more than a mV) different from zero. The audio tone signals include tone signals separated by time intervals (spaces).

Still another object of the invention is to provide a device for assisting a blind individual by presenting the individual with audio, white noise, pink noise, brown noise, popcorn noise signals, audio tone signals or some combination thereof, along with a proximity sensory signal to assist the individual in determining their relative position to other objects.

These and other objects of the present invention are achieved by providing an apparatus which includes a sensor which senses a motion of an object and a sensory converter which converts the sensed motion to corresponding sensory signals. In addition, the sensory signals are presented to a user by using, for example, a transmitter and receiver. Thus, the user receives the sensory signals and is able to resolve a conflict between vestibular, ocular, and proprioceptive inputs via the principle of indeterminancy. The sensory signals may be any one of audio, white noise, pink noise, brown noise, popcorn noise, display signals, audio tones, or any combination thereof. The audio, white noise, pink noise, brown noise and popcorn noise sensory signals have a variation in a spectral emphasis in proportion to the sensed motion. In the case of audio signals, the variation in spectral emphasis includes varying a frequency of, for example, a first signal within a first predetermined range around a first center frequency in proportion to a sensed pitching motion of the object. For the case of white noise, pink noise, brown noise, and popcorn noise signals, the variation in spectral emphasis includes varying, for example, a first frequency range of the noise signals in proportion to a sensed pitching motion of the object. However, in all cases for audio, white noise, pink noise, brown noise and popcorn noise signals, the variation in spectral emphasis may include, but is not limited to, a variation in a bandwidth, a center frequency, and an amplitude of first range of the sensory signals. In addition, the display signals may be presented on a display as display elements which vary in a display characteristic based on the sensed motion of the object. The variation in display characteristic includes a variation in, for example, a shape, a size, a color, and an intensity of the display element. In the case of audio tone signals, the audio tone signals may have a variation in time intervals between successive audio tones based on the sensed motion of the object.

BRIEF DESCRIPTIONS OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
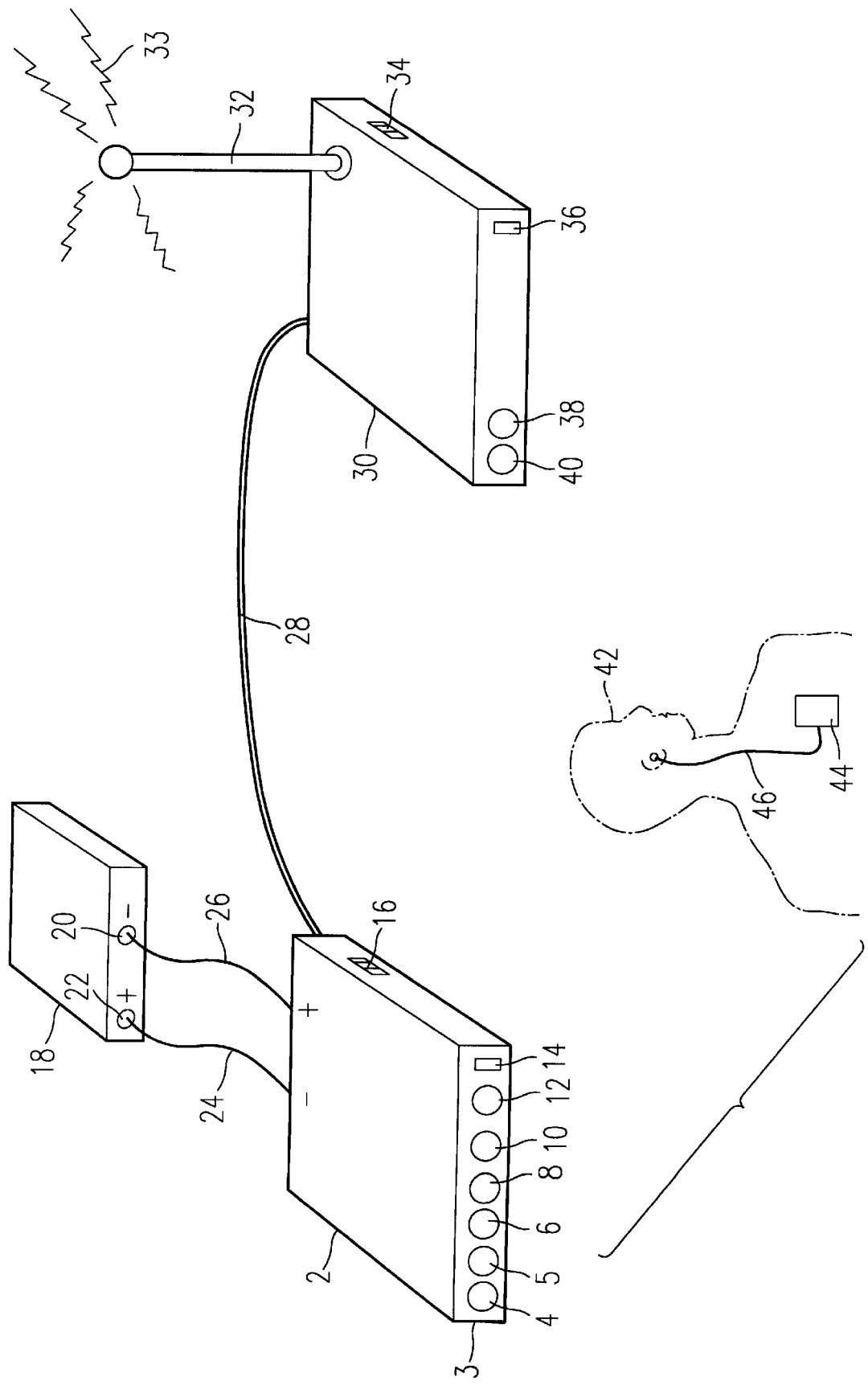
FIG. 1 is a perspective view of an apparatus for relieving motion sickness according to the present invention.

Referring now to the drawings, wherein like reference numerals designate identical or corresponding parts throughout the several views, and more particularly to FIG. 1 thereof, there is illustrated an apparatus for relieving motion sickness including an inertia processor 2 connected to an external battery 18 and a transmitter 30. Also shown is a receiver 44 attached to an individual 42 for receiving a sensory signal 33 transmitted by the transmitter 30. The inertia processor 2 includes a front panel 3 which houses an audio volume control mechanism 4, a video control mechanism 5, a white, pink, brown or popcorn noise volume control mechanism 6, a pitch (x-axis) sensitivity control mechanism 8, a yaw (y-axis) sensitivity control mechanism 10, and a vertical (z-axis) sensitivity control mechanism 12. The inertia processor also includes an appropriate bandpass filter (now shown) to achieve a desired bandwidth of the sensory signals.

The audio volume mechanism 4 and the white, pink, brown or popcorn noise volume mechanism 6 may be used to adjust the volume of the sensory signal 33 transmitted by the transmitter 30. The pitch sensitivity mechanism 8, the yaw sensitivity mechanism 10, and the vertical sensitivity mechanism 12 may be used to adjust the corresponding sensitivity of the inertia processor 2. That is, using these sensitivity mechanisms, a user may set the inertia processor 2 to be more or less sensitive in sensing a motion of an object. Also included in the front panel 3 is an LED power indicator 14 which indicates whether the power is on or off. For example, if the power is on, the LED indicator 14 will be a green color. On a side portion of the inertia processor 2 is a power switch 16 used to turn on and off the inertia processor 2. The inertia processor 2 also includes three RCA autojacks on a rear side of the instrument (not shown) which provide high impedance, low level output for audio, video, white noise, pink noise, brown noise, popcorn noise and audio tone signals.

The battery 18 includes a negative battery terminal 20 and a positive battery terminal 22 which connect to the inertia processor 2 via battery wires 24 and 26. In addition, the inertia processor 2 is connected to the transmitter 30 using a communication cable 28. Alternatively, the inertia processor 2 may be optically connected (e.g., using infrared signals) to the transmitter 30. The transmitter 30 includes an antenna 32, a power switch 34, and a power LED indicator 36. Also included is, for example, a multichannel control mechanism 38 and a volume control mechanism 40.

The control mechanisms (e.g., volume control mechanisms 4 and 6) are not limited to the locations shown in FIG. 1. For example, the volume control mechanisms 4 and 6 may be placed on a side or top portion of the inertia processor 2. Further, the battery 18, inertia processor 2, transmitter 30, and receiver 44 may be included in a single common housing.

The inertia processor 2 may be mounted or placed on a level (normally level) surface of an object. The inertia processor 2 senses a motion of the object and converts this motion to corresponding sensory signals for presentation to a user. The audio, white noise, pink noise, brown noise, and popcorn noise sensory signals have a variation in spectral emphasis in proportion to the sensed motion. The variation in spectral emphasis includes, but is not limited to, a variation in a bandwidth, a center frequency, and an amplitude of a first range of the sensory signals. For example, if the inertia processor 2 is configured to operate using audio signals, i.e., by connecting the audio output jack of the inertia processor 2 to the transmitter 30, the variation in spectral emphasis includes varying a frequency of, for example, a first signal within a first predetermined range around a first center frequency in proportion to a sensed pitching motion of the object. Alternatively, if the inertia processor 2 is configured to operate using white, pink, brown or popcorn noise signals, the variation in spectral emphasis includes varying, for example, a first frequency range of the white, pink, brown or popcorn noise signals in proportion to a sensed pitching motion of the object. In addition, if the inertia processor 2 is configured to operate using display signals, the display signals may be displayed as display elements which have a variation in a display characteristic corresponding to the sensed motion of the object. The display elements may include, for example, red, green, and blue colors used in a conventional video display. The red, green and blue colors are altered in proportion to the sensed motion of the object. Finally, if the inertia processor 2 is configured to operate using audio tone signals, the audio tone signals may have a variation in time intervals between successive audio tones based on the sensed motion of the object.

The sensory signals sensed by the inertia processor 2 are presented to the user 42 using, for example, the transmitter 30 and receiver 44. The receiver 44 may be, for example, a pocket-sized receiver, in order to receive the sensed sensory signals 33. The receiver 44 also includes, for example, an earphone 46 so the user may listen to the corresponding sensory signals. The user 42 then uses the sensory signals 33 transmitted by the transmitter 30, without conscious volition, to resolve a conflict between the vestibular, ocular, and propreoceptive inputs, thereby relieving a sense of motion sickness.

In addition, it should be noted that FIG. 1 illustrates the sensed sensory signals being presented to the user 42 with a transmitter 30 and receiver 44. However, it is also possible to present the sensory signals sensed by the inertia processor 2 directly to the user 42 by using an earphone, for example, connected to the inertia processor 2. That is, the use of a separate transmitter 30 and receiver 44 is not required.

Figure 2:
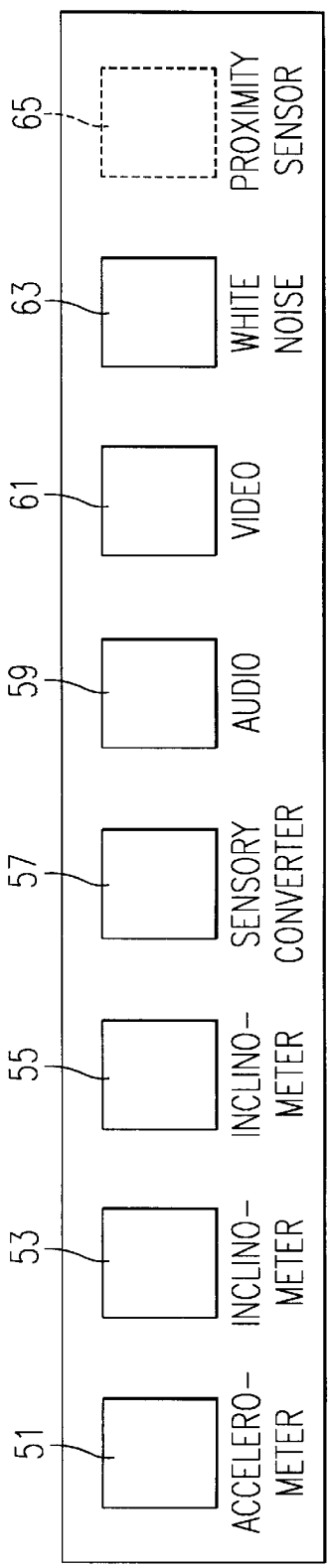
FIG. 2 is a block diagram illustrating the components of an inertia processor device according to the present invention.

FIG. 2 illustrates a block diagram of the components contained within the inertia processor 2. As shown, the inertia processor 2 includes an accelerometer 51, a first inclinometer 53, a second inclinometer 55, a sensory converter 57, an audio processor 59, a video processor 61, a white, pink, brown or popcorn noise processor 63, and optionally a proximity sensor 65.

Figure 10:
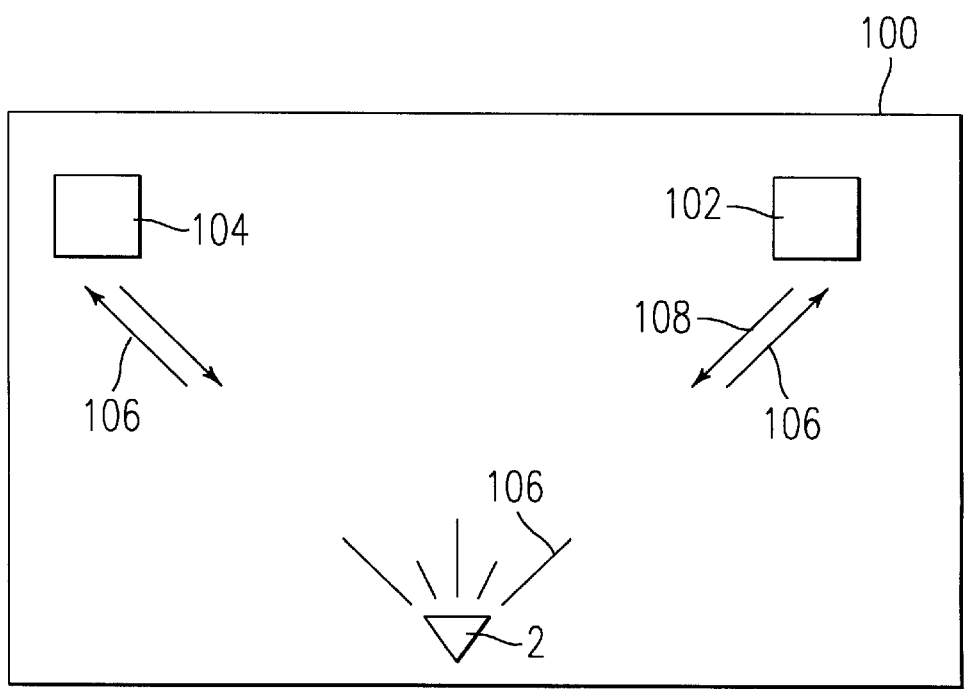
FIG. 10 is another perspective view of the motion sickness device used to assist an eyesight impaired individual.

The accelerometer 51, and inclinometers 53 and 55 may be those which are commercially available. The accelerometer 51 senses a vertical motion of an object, the first inclinometer 53 senses a yaw motion of the object, and the second inclinometer 55 senses a pitching motion of the object. The sensory converter 57 converts this sensed motion to corresponding sensory signals for presentation to the user. The audio processor 59 communicates the sensory signals as audio signals or audio tones to the transmitter 30. Similarly, the video processor 61 and noise processor 63 communicate the sensory signals as video signals and white, pink, brown or popcorn noise signals, respectively, to the transmitter 30. In addition, the inertia processor 2 may include an additional accelerometer and a third and fourth inclinometer so that the inertia processor may detect a motion in at least one of six degrees of freedom. The inclinometers and accelerometers function as a sensor which detect a motion of the object. Further, the inertia processor 2 may optionally include a proximity sensor 65. The proximity sensor 65 determines relative locations of other objects with respect to the inertia processor 2 (e.g., by using lasers, or capacitive sensor systems). Thus, a blind person may wear the inertia processor 2 including the proximity sensor 65 and receive audio signals corresponding to the determined relative position of other objects. This feature is shown in FIG. 10 and will be discussed later.

Figure 3:
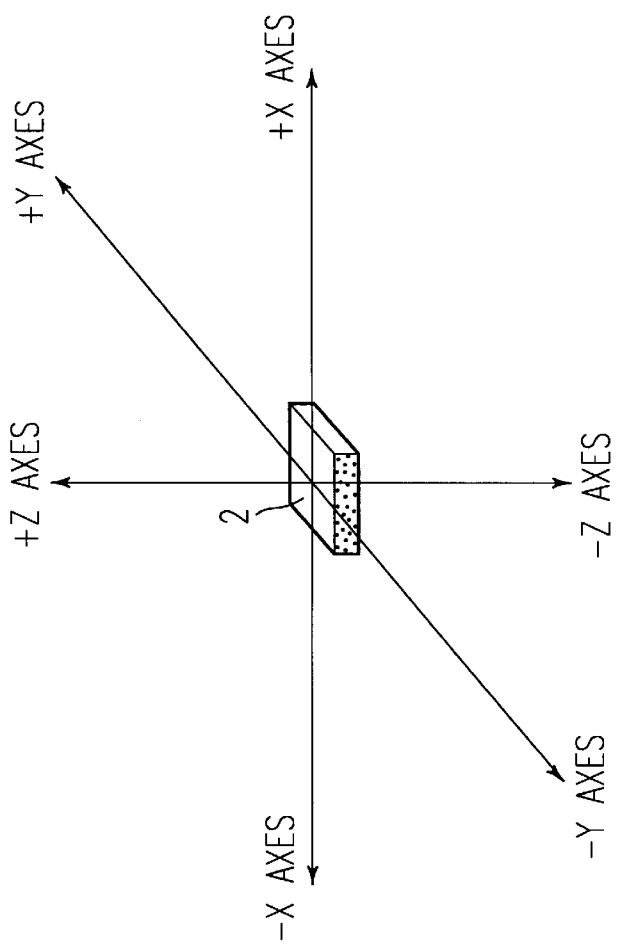
FIG. 3 illustrates a three-dimensional axis with respect to the inertia processor according to the present invention.

FIG. 3 illustrates a three-dimensional axis with respect to the inertia processor 2 shown in FIG. 2. The accelerometer 51 senses a vertical motion of the object along the vertical axis, designated as the z-axis. The inclinometers 53 and 55 detect inclination changes (i.e., pitching and yawing motions) about the horizontal plane designated as the x-axis and yaxis, respectively.

Figure 4A:
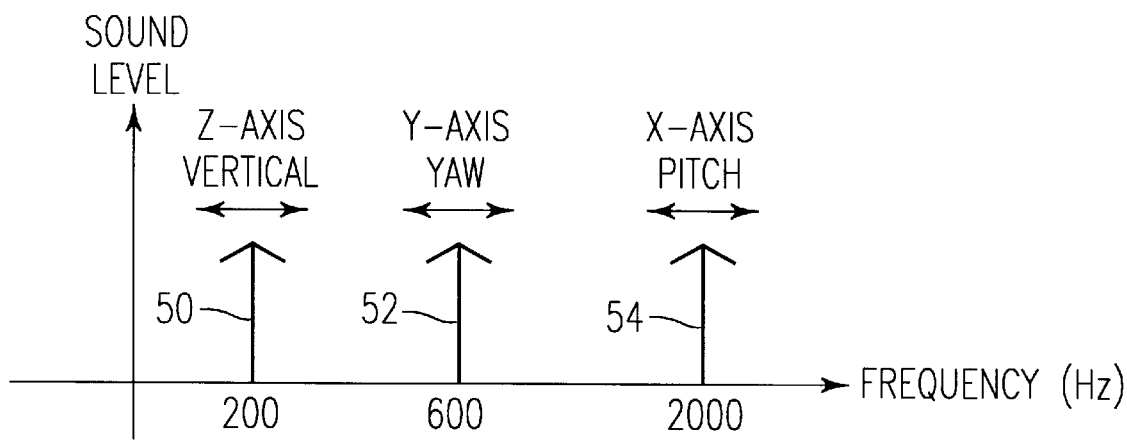
FIG. 4A is a graph illustrating frequencies of audio signals corresponding to vertical, yaw, and pitch motions sensed by the inertia processor shown in FIG. 3.

FIG. 4A illustrates audio signals in response to motion sensed by the inertia processor 2. As shown, the inertia processor 2 generates three different audio signals which individually change in frequency in response to a sensed motion. The z-axis frequency tone 50, which may be centered at 250 Hz, for example, increases in frequency when a positive z-axis motion is sensed and decreases in frequency in response to a negative z-axis sensed motion. The z-axis vertical tone 50 shown in FIG. 4A is at 200 Hz, which represents a decrease of 50 Hz from the center frequency.

That is, a negative z-axis motion was sensed by the accelerometer 51. The y-axis frequency tone 52, centered at 500 Hz, for example, increases in frequency when the instrument is tilted clockwise (when viewed from the front of the device) about the y-axis. This is referred to as a yaw to the right. In addition, the y-axis frequency tone 52 decreases in frequency when the instrument is tilted counter-clockwise about the y-axis, referred to as a yaw to the left. The y-axis frequency tone 52 shown in FIG. 4A is at 600 Hz, which represents an increase of 100 Hz from the center frequency. That is, a yaw to the right was sensed by the inclinometer 53. The x-axis frequency tone 54, centered at 2 KHz, for example, increases in frequency when the instrument is tilted forward, referred to as a forward pitch, and decreases in frequency when the instrument is tilted backwards, referred to as a rearward pitch. Thus, as shown, the x-axis frequency tone 54 has not changed, which indicates the second inclinometer 55 did not detect a pitching motion. In addition, the changes to the tone frequencies are proportional to the sensed motion, that is, the greater the sensed motion, the greater the tone change. However, the proportional relationship is not necessarily linear and may be empirically determined. The representation of the center tone frequencies of 250 Hz, 500 Hz, and 2 KHz are for illustration purposes only and other values may be used.

Figure 4B:
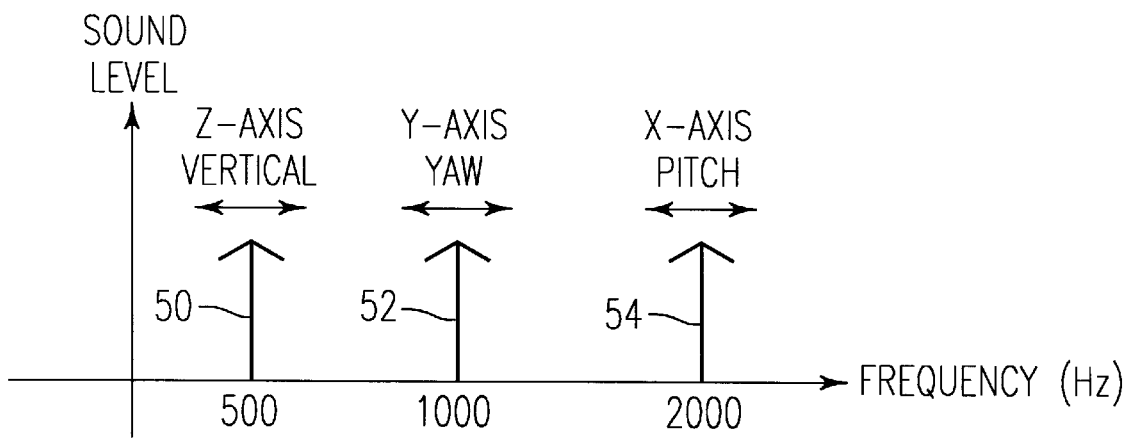
FIG. 4B is another graph illustrating frequencies of audio signals corresponding to vertical, yaw, and pitch motions sensed by the inertia processor shown in FIG. 3.

For example, FIG. 4B illustrates the z-axis frequency tone 50, the y-axis frequency tone 52, and the x-axis frequency tone 54 centered at frequencies of 500, 1000, and 2000 Hz, respectively. The frequency tones increase and decrease in response to a sensed motion, as described in reference to FIG. 4A. Through experimentation, it has been determined that the human ear is particularly sensitive to frequencies around 1000 Hz. Further, it has been determined that the y-axis yaw motion is particularly critical in causing motion sickness. Therefore, in FIG. 4B, the y-axis frequency tone 52 (i.e., y-axis yaw motion) is centered at 1000 Hz.

Further, FIGS. 4A and 4B correspond to motion sensed in three degrees of freedom. As discussed above, the inertia processor 2 may detect motion in at least six degrees of freedom. Thus, if six degrees of freedom were sensed, it is possible to represent this by six tones rather than three tones.

Figure 5A:
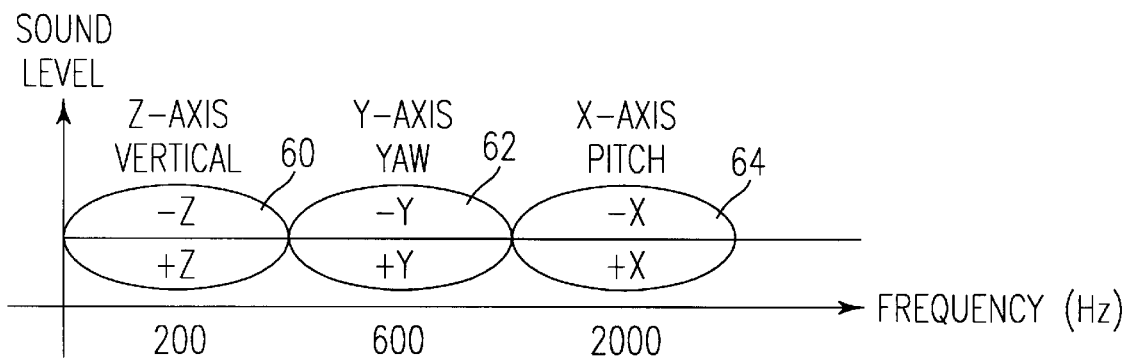
FIG. 5A is a graph illustrating frequency ranges of a white noise signal corresponding to vertical, yaw and pitch motions sensed by the inertia processor shown in FIG. 3.

FIG. 5A is similar to FIG. 4A but illustrates a white noise frequency spectrum in response to motion sensed by the inertia processor 2. In addition, as discussed above, pink, brown or popcorn noise signals may also be used. As shown, the spectral component of the white noise frequency spectrum is divided into three frequency ranges. The white noise frequency spectrum includes a z-axis vertical frequency range 60, a y-axis yaw frequency range 62, and an x-axis pitch frequency range 64. The amplitude of these frequency ranges are altered by the inertia processor 2 in response to the sensed motion. A positive z-axis sensation decreases the amplitude of the z-axis vertical frequency range 60. A negative z-axis sensation increases the amplitude of the z-axis vertical frequency range 60. A yaw to the right decreases the amplitude of the y-axis yaw frequency range 62 and a yaw to the left increases the amplitude of this range. Similarly, a forward pitch results in a decrease of the amplitude of the x-axis pitch frequency range 64 and a rearward pitch results in an increase in amplitude of this frequency range. In addition, the changes to the amplitudes of the frequency ranges of the white noise are proportional to sensed motion, that is, the greater the sensation, the greater the spectral amplitude change. Again, the proportional relationship is not necessarily linear.

Figure 5B:
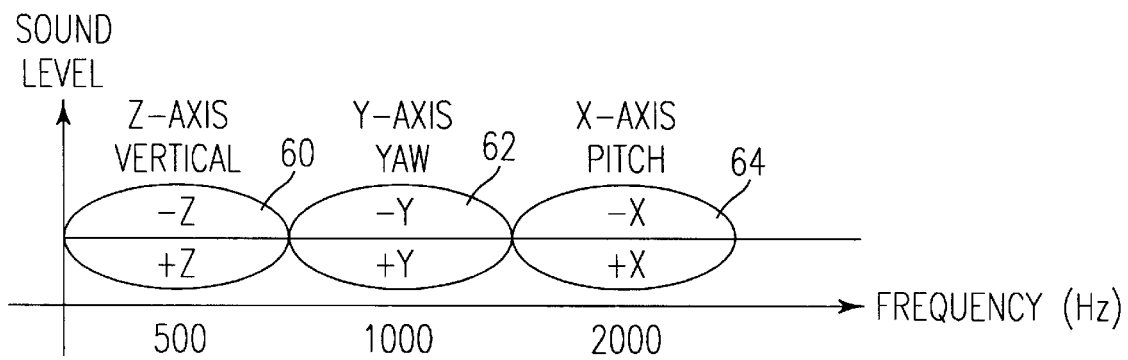
FIG. 5B is another graph illustrating frequency ranges of a white noise signal corresponding to vertical, yaw and pitch motions sensed by the inertia processor shown in FIG. 3.

FIG. 5A illustrates the z-axis vertical frequency range 60, y-axis yaw frequency range 62, and x-axis pitch frequency range 64 centered at 200 Hz, 600 Hz, and 2 KHz, respectively. However, these ranges may be centered at other frequencies. For example, FIG. 5B illustrates the z-axis vertical frequency range 60, the y-axis yaw frequency range 62, and the xaxis pitch frequency range 64 centered at frequencies of 500 Hz, 1000 Hz, and 2000 Hz, respectively. The amplitude of these frequency ranges are altered by the inertia processor 2 in response to a sensed motion, as described in reference to FIG. 5A. Further, the y-axis yaw frequency range 62 is centered at 1000 Hz for similar reasons as that discussed in reference to FIG. 4B. That is, the yaw motion is particularly critical in causing motion sickness and the human ear is particulary sensitive to frequencies around 1000 Hz.

Figure 5C:
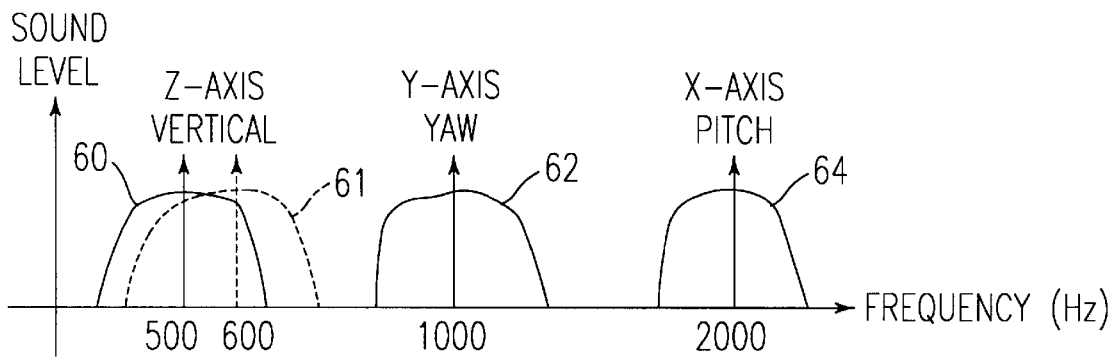
FIG. 5C is yet another graph illustrating frequency ranges of a white noise signal corresponding to vertical, yaw and pitch motions sensed by the inertia processor shown in FIG. 3.

FIG. 5C is yet another graph illustrating frequency ranges of a white noise signal corresponding to vertical, yaw, and pitch motions sensed by the inertia processor shown in FIG. 3. In particular, FIG. 5C is similar to FIGS. 5A and 5B except that a center frequency of the z-axis vertical frequency range 60, y-axis yaw frequency range 62, and x-axis pitch frequency range 64 shift in response to a sensed motion. That is, the center frequency of the z-axis vertical frequency range 60 (e.g., centered at 500 Hz) increases in frequency when a positive z-axis motion is sensed and decreases in frequency in response to a negative z-axis sensed motion. The z-axis vertical frequency range 61 (illustrated by a dotted line) represents that the z-axis vertical frequency range 60 has been shifted from a center frequency of 500 Hz to a center frequency of 600 Hz. This shift indicates the inertia processor 2 sensed a positive z-axis motion. That is, a positive z-axis motion was sensed by the accelerometer 51. The center frequency of the y-axis yaw frequency range 62 (e.g., centered at 1000 Hz) increases in frequency when the inertia processor 2 is tilted clockwise (when viewed from the front of the device) about the y-axis (i.e., yaw to the right). In addition, the center frequency of the y-axis yaw frequency range 62 decreases in frequency when the inertia processor 2 is tilted counterclockwise about the y-axis (i.e., yaw to the left). The y-axis yaw frequency range 62 shown in FIG. 5C is centered at 1000 Hz, which represents a yaw to the right, was not sensed by the inclinometer 53 (i.e., the frequency range did not shift). The center frequency of the x-axis pitch frequency tone 64 (e.g., centered at 2 KHz) increases in frequency when the instrument is tilted forward, referred to as a forward pitch, and decreases in frequency when the instrument is tilted backwards, referred to as a rearward pitch. Thus, as shown, the x-axis pitch frequency range 64 has not changed, which indicates the second inclinometer 55 did not detect a pitching motion. In addition, the changes to the frequencies ranges are proportional to the sensed motion, that is, the greater the sensed motion, the greater the change of the frequency range. The sound level (i.e., amplitude) of each frequency range may also be adjusted as described in reference to FIGS. 5A and 5B.

Figure 5D:
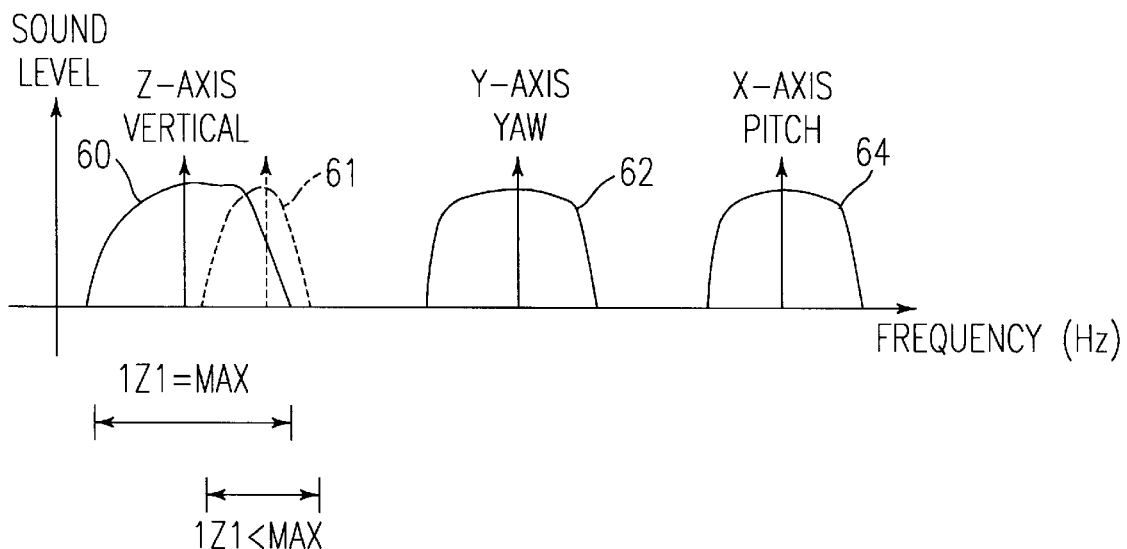
FIG. 5D is still another graph illustrating frequency ranges of a white noise signal corresponding to vertical, yaw and pitch motions sensed by the inertia processor shown in FIG. 3.

FIG. 5D is still another graph illustrating a variation of frequency ranges of a white noise signal corresponding to vertical, yaw and pitch motions sensed by the inertia processor 2. FIG. 5D is similar to FIGS. 5B and 5C, but a bandwidth of the z-axis vertical frequency range 60, y-axis yaw frequency range 62, and x-axis pitch frequency range 64 also shift in response to a sensed motion. That is, based on a detection motion, the bandwidth may increase or decrease. Thus, for the case of FIG. 5D, the variation in spectral emphasis includes a variation in a bandwidth, a center frequency, and an amplitude of a first range of the sensory signals. For example, as illustrated in FIG. 5D, when the inertia processor 2 senses z-axis vertical data indicating a steady state (i.e., normally level) motion, the bandwidth of the z-axis vertical frequency range 60 is a maximum ($|z|$=max). When the inertia processor 2 senses an increase in the z-axis vertical motion, the bandwidth of the z-axis vertical frequency range 60 decreases ($|z|$<max). The decrease in the bandwidth of the z-axis vertical frequency range is illustrated as a z-axis vertical frequency range 61. Therefore, FIG. 5D illustrates an example of adjusting a bandwidth, a center frequency, and a sound level of the z-axis vertical frequency range 60. Likewise, the y-axis yaw vertical range 62 and the x-axis pitch vertical range 64 may be adjusted.

Further, the bandwidth of the frequency ranges may be selected different than that shown in FIGS. 5A, 5B, 5C, and 5D. In addition, FIGS. 5A, 5B, 5C, and 5D correspond to motion sensed in three degrees of freedom. However, as discussed above, the inertia processor 2 may detect motion in at least six degrees of freedom, and accordingly it is possible to represent these six degrees of freedom by using six frequency ranges of the white noise signal. Further, pink, brown and popcorn noise signals may be used rather than white noise signals.

Figure 6:
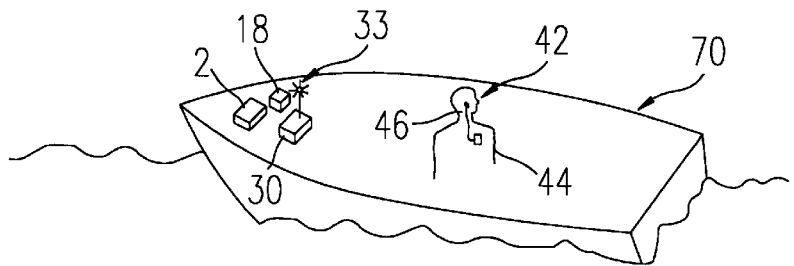
FIG. 6 is a perspective view of the motion sickness apparatus used aboard a ship.
Figure 9:
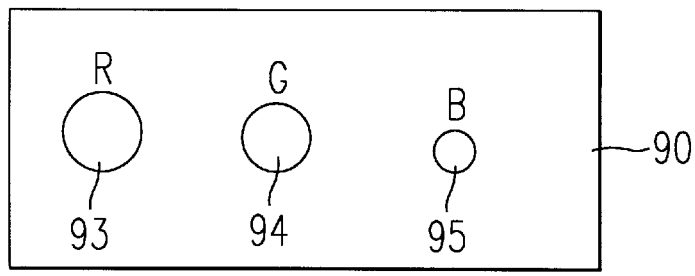
FIG. 9 is yet another perspective view of the motion sickness device used to project a display signal including display elements on a display.
Figure 9:
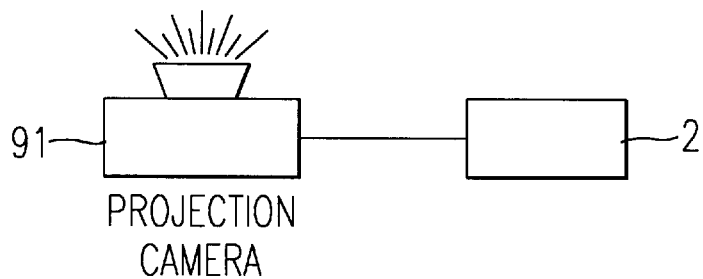
Figure 11A:
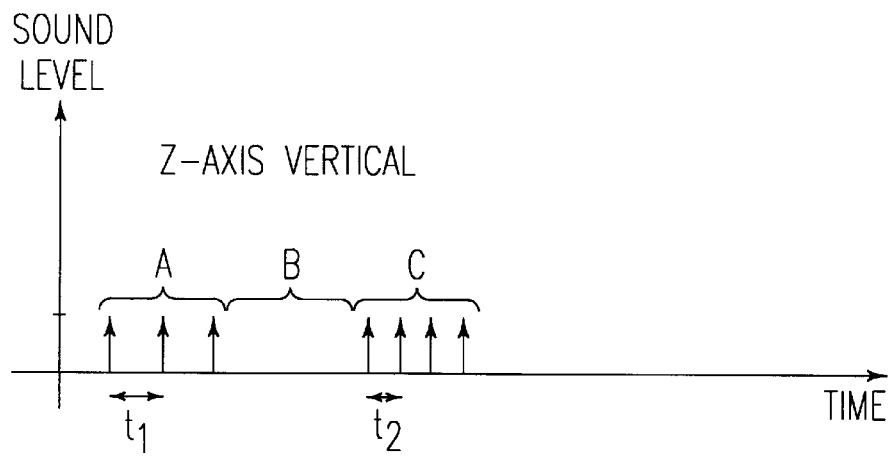
FIG. 11A is a graph illustrating audio tone signals corresponding to a vertical motion sensed by the inertia processor shown in FIG. 3.
Figure 11B:
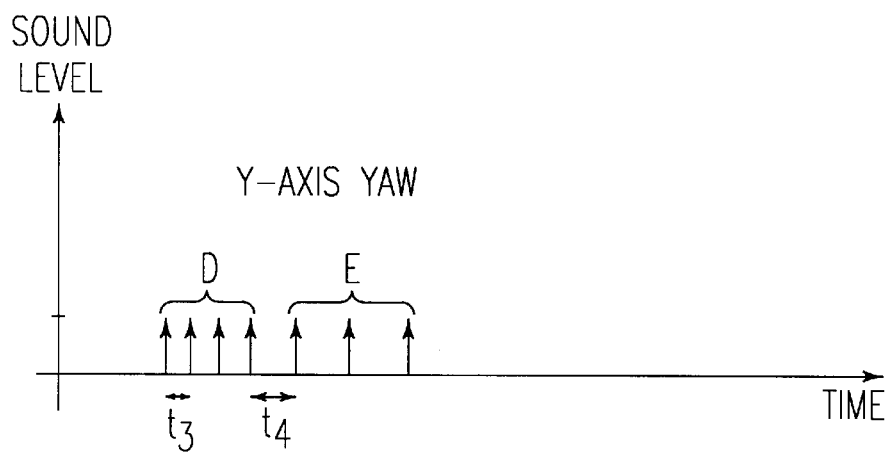
FIG. 11B is another graph illustrating audio tone signals corresponding to a yaw motion sensed by the inertia processor shown in FIG. 3.
Figure 11C:
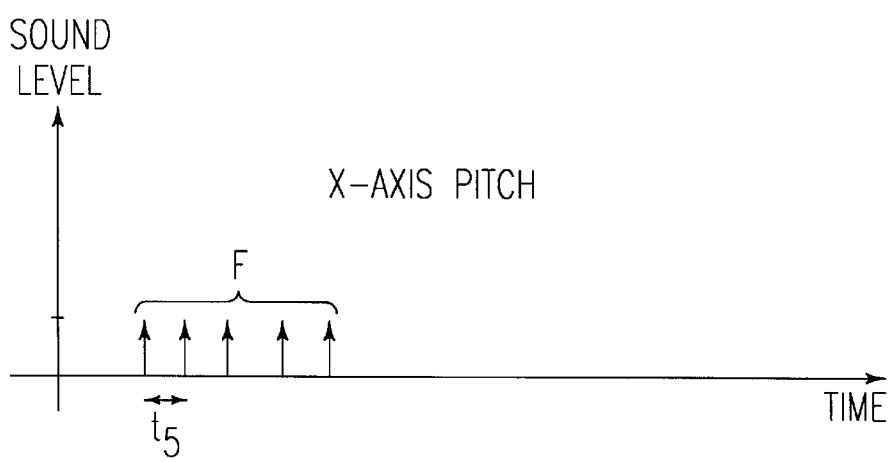
FIG. 11C is yet another graph illustrating sensory signals corresponding to a pitch motion sensed by the inertia processor shown in FIG. 3.

To operate the device of the present invention, the inertia processor 2 may be mounted or placed on a level (normally level) surface of an object and connected to the transmitter 30. One example of using the device of the present invention is that shown in FIG. 6. As shown, the inertia processor 2, battery 18, and transmitter 30 are mounted securely in a bow of a boat 70. When the boat 70 moves, the inertia processor 2 senses this motion and converts the sensed motion into corresponding sensory signals. The sensory signals 33 are then transmitted to the receiver 44 which is attached to the user 42. The user 42 hears the sensory signals 33 using, for example, an earphone 46. Thus, the user will, without conscious volition, utilize this accurate new data stream to resolve the conflict between the various ocular, vestibular and proprioceptive inputs via the principle of indeterminacy. The sensory signals 33 may be audio, display, white noise, pink noise, brown noise, popcorn noise, audio tones or any combination thereof An example of using display signals is shown in FIG. 9 and will be described later. Further, an example of using audio tones is shown in FIGS. 11A–11C and also will be described later.

Figure 7:
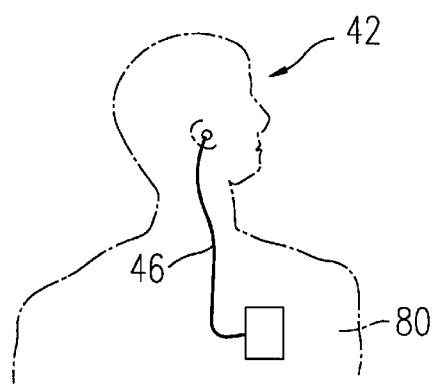
FIG. 7 is a perspective view of the motion sickness apparatus attached to an individual.

FIG. 7 illustrates another use of the device according to the present invention. In this example, the inertia processor 2, battery 18, transmitter 30, and receiver 44 are contained in a single common housing 80. The inertia processor 2 is similar to that shown in FIG. 2, but includes only the first inclinometer 53 and second inclinometer 55, which detect yaw and pitch motions, respectively (i.e., the accelerometer 51 is not included). Thus, the inertia processor 2 contained in the common housing 80 senses changes in the individual's motion (i.e., y-axis yaw and x-axis pitch motions), converts this sensed motion to corresponding sensory signals, and presents the sensory signals to the user. Further, the device may be placed at various points on the body to accurately reflect positional changes, such as a plurality of sensors placed along the individual's spine.

Figure 8:
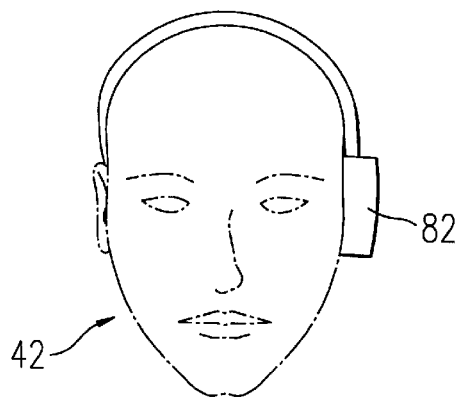
FIG. 8 is another perspective view of the motion sickness apparatus included in a headphone.

FIG. 8 illustrates yet another example in which the device of the present invention may be used. In this example, the inertia processor 2, battery 18, transmitter 30, and receiver 44 are included in a headset so that the movement of the head is sensed rather than the movement of the body. The inertia processor 2 is similar to that discussed for FIG. 7 and senses motion in 2 axes (i.e., yaw and pitch). This illustration is particular useful for individuals which have severe balancing problems. In fact, some individuals with a severe vestibular imbalance become nauseated at the slightest movement of their head. This device can assist that individual in reconciling the conflicts between received vestibular and ocular data.

FIG. 9 illustrates another example in which the device may be used. In this example, the inertia processor 2 senses the motion of an object and converts this sensed motion into first, second and third display signals to be displayed as corresponding first, second and third displayed elements on a video display 90. The converted display signals corresponding to the sensed motion is output to, for example, a projection camera 91 via the audio jack of the inertia processor 2. The projection camera 91 projects the display signals as corresponding displayed elements to the video display 90, which a single user or multiple users may be viewing while being aboard, for example, a ship. The displayed elements may be a variety of colors, each color corresponding to a particular sensed motion. For example, the red, green, and blue colors in a conventional color scheme may correspond to a sensed vertical, yawing, and pitching motion of the object, with the selected colors varying in a display characteristic in proportion to the sensed motion. For example, the red (R) displayed element 93, green (G) displayed element 94, and blue (B) displayed element 95 shown in FIG. 9 may vary, for example, in at least one of intensity, pattern, size, and shade of color based on the respective sensed vertical, yawing, and pitching motion of the object. The displayed elements 93, 94 and 95 are illustrated in FIG. 9 as circles. However, the displayed elements 93, 94 and 95 may be any symbol, such as a star-shaped symbol, a square-shaped symbol, etc. As shown, the blue (B) displayed element 95 has decreased in size based on a sensed vertical motion (for example, due to a negative pitching motion of the ship). Another example of presenting display signals, which have been converted from sensed motions by the inertia processor, may be achieved by displaying a column of display elements on a left portion of a video display and a row of display elements on a bottom portion of the video display. The column of displayed elements may appear to the viewer as moving vertically in either direction, and the row of displayed elements may appear as moving horizontally in either direction. The column of displayed elements may correspond to the sensed vertical motion and the row of displayed elements may correspond to the sensed yawing motion. The speed and direction that the displayed elements move is based on the sensed motion of the ship. In addition, for the sensed pitching motion, a displayed element which includes a circle with a dot in the center may be displayed in a middle portion of the video display. In this case, the circle may become larger or smaller based on a sensed pitching motion of the stern of the boat, whereas the dot in the center may move up or down, for example, based on a sensed pitching motion of the bow of the boat.

Thus, the individual user or multiple users viewing the display, can use the displayed elements to reconcile a conflict between the vestibular, ocular, and proprioceptive inputs, thus reducing the likelihood of motion sickness. Similarly, a displayed element representing an actual ship, for example, as in a view directly forward from the bow will also accomplish this same conflict resolution.

FIG. 10 illustrates another example in which the device of the present invention may be used. In this example, the device is used to assist a blind person. Essentially, if one closes their eyes and walks around a room, it is not particularly difficult to maintain a vertical position. Their proprioceptive receptors and to some extent their vestibular receptors may be termed an experimental data base, which allows them to understand where they are relative at least to an upright position. But if an individual has been blind since birth, they would not have access to this experimental data base. The device according to the present invention is used to expand this data base. By verifying where an individual's body is relative to the ground and other objects, the individual in question could move about with more confidence. Thus, by using the proximity sensor 65 (shown in FIG. 2), the individual will have an added ability to assert their position relative to other objects.

In more detail, FIG. 10 illustrates a room 100 in which a blind person (not shown) is wearing the inertia processor 2 included in the common housing 80 shown in FIG. 7, for example. Also shown are objects 102 and 104 which may be furniture, another person, etc. Thus, as the individual walks about the room, the proximity sensor 65 transmits, for example, laser signals 106. The laser signals 106 are then reflected off the objects 102 and 104. For example, as shown, a reflected signal 108 is reflected off the object 102. The inertia processor 2 receives this reflected signal 108 and converts it to sensory signals. The sensory signals have a spectral emphasis which varies in proportion to the distance of the sensed objects relative to the blind individual. For example, if the object 102 is very close, a high pitch tone may be generated, whereas if the object 102 in far away, and low pitch tone may be used. The variation in spectral emphasis includes, but is not limited to, a variation in a bandwidth, a center frequency, and an amplitude of a first range of the sensory signals.

FIGS. 11A–11C illustrate audio tone signals in response to respectively sensed vertical, yaw and pitch motions of an object. For example, as shown in FIG. 11A, the audio tones shown in portion A have a time interval $t_1$. Further, the portion B does not contain audio tones and thus the user would not hear any audio tones. The portion C includes audio tones which are separated by a time interval $t_2$. The audio tone signals shown in portion A may be 500 Hz and the audio tone signal shown in portion C may be 550 Hz, for example. The audio tone signals in portion A correspond to a negative detected z-axis vertical motion and the tone signals shown in portion C correspond to a positive detected z-axis vertical motion. Thus, as shown in FIG. 11A, the user hears the tone signals in portion A separated by time intervals $t_1$ which is due to a negative z-axis vertical detected motion. Then as the object achieves a substantially stable position, the user will hear silence which is illustrated as portion B in the figure. That is, the tone signals only occur when a motion of the object is sensed by the inertia processor 2. Thus, if the object is not moving, the user will not be inundated with tone signals. Further, the tone signals in portion C, which correspond to a positive detected z-axis vertical sense motion, have a smaller time interval $t_2$ than the tone signals in portion A (time intervals $t_1$). The tone signals in portion C have a shorter time interval based on a larger degree of the detected z-axis vertical motion. For example, if a large z-axis vertical motion is detected, the time interval $t_2$ is made shorter so that the user will hear more tone signals than if a smaller z-axis vertical motion is detected. Alternatively, the time intervals may be set to be opposite of that discussed above. That is, the tone signals may be set so that the interval therebetween is larger based on a larger sensed motion.

FIGS. 11B and 11C are similar to FIG. 11A but correspond to y-axis yaw sensed motion and x-axis pitch sensed motion. The tone signals shown in portion D of FIG. 11B may be 1,000 Hz and are separated by a time interval $t_3$. The tone signals shown in portion E may be 1,100 Hz are separated by a time interval $t_4$ The audio tone signals shown in portion F of FIG. 11C may be 2,000 Hz and are separated by a time interval $t_5$. Obviously, alternative frequencies and time intervals can be used for the audio tones. Thus, as shown in FIGS. 11A–11C, as the motion of the object is detected, a plurality of audio tones are intermittently supplied to the user based on the sensed motion of the object.

In addition, it is to be understood that the audio tones may also be audio messages, such as words. For example, the audio tones may be words, such as "left, left, left . . . right, right, right" that are presented to the user based on the sensed motion of the object. The interval between the words may also vary as that described for the audio tones.

A method of relieving motion sickness will now be described with reference to FIGS. 1, 3 and 4. The inertia processor 2 is used for sensing a motion of an object and for converting the sensed motion to corresponding sensory signals. As discussed above, the audio, white noise, pink noise, brown noise and popcorn noise sensory signals have a variation in spectral emphasis in proportion to the sensed motion. In addition, the display signals have a variation in a display characteristic and the audio tone signals have a variation in time intervals between successive audio tones based on the sensed motion of the object. Further, the method of converting includes presenting the sensory signals using, for example, the transmitter 33 and the receiver 44. In one example, the method of converting includes varying a frequency of a first signal within a first predetermined range around a first center frequency in proportion to a sensed pitching motion of the object, and varying a frequency of a second signal within a second predetermined range around a second center frequency in proportion to a sensed yawing motion of the object. In another example, the method of converting includes varying a spectral emphasis of a first frequency range of white, pink, brown or popcorn noise signals in proportion to a sensed pitching motion of the object, and varying a spectral emphasis of second frequency range of the white, pink, brown or popcorn noise signals in proportion to a sensed yawing motion of the object. The variation in spectral emphasis includes, but is not limited to, a variation in a bandwidth, a center frequency, and an amplitude of a first range of the sensory signals. In addition, the method of converting also includes generating display elements which correspond to the sensed sensory signals. For the case of display signals, the display signals vary in a display characteristic in proportion to the sensed motion of the object. The method of converting also includes generating audio tone signals which correspond to the sensed sensory signals. For the case of the audio tone signals, the audio tone signals have a variation in time intervals between successive audio tones based on the sensed motion of the object.

Further, the present inventor has determined that low frequency horizontal movements appear to be most related to motion sickness. By providing a device which includes a sensor to detect these movements, and a sensory converter coupled to the sensor, as discussed above, the present invention reduces the effect of motion sickness.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent in the United States is:

1. An apparatus for relieving motion sickness, comprising:
   at least one sensor which senses a motion of an object;
   a sensory converter coupled to said sensor and configured to convert said sensed motion to corresponding sensory signals having a variation in spectral emphasis in proportion to said sensed motion, comprising:
   a first mechanism configured to vary said spectral emphasis including at least one of 1) a bandwidth and 2) a center frequency of a first frequency range of said sensory signals in proportion to a sensed pitching motion of said object, and
   a second mechanism configured to vary said spectral emphasis including at least one of 1) a bandwidth and 2) a center frequency of a second frequency range of said sensory signals in proportion to a sensed yawing motion of said object; and
   a presentation mechanism configured to present said sensory signals to a user.

2. The apparatus according to claim 1, wherein said first mechanism varies an amplitude of said first frequency range of said sensory signals in proportion to a sensed pitching motion of said object, and said second mechanism varies an amplitude of said second frequency range of said sensory signals in proportion to a sensed yawing motion of said object.

3. The apparatus according to claim 1, wherein said sensory converter further comprises:
   a third mechanism configured to vary said spectral emphasis including at least one of 1) a bandwidth, 2) a center frequency, and 3) an amplitude of a third frequency range of said sensory signals in proportion to a sensed vertical motion of said object.

4. The apparatus according to claim 1, wherein said sensory converter further comprises:
   a third mechanism configured to generate at least one of 1) white noise signals, 2) pink noise signals, 3) brown noise signals, 4) popcorn noise signals, and 5) display signals which correspond to said sensory signals.

5. The apparatus according to claim 1, wherein said first mechanism varies said center frequency of said first frequency range from an initial center frequency of approximately 2000 Hz, and said second mechanism varies said center frequency of said second frequency range from an initial center frequency of approximately 1000 Hz.

6. The apparatus according to claim 3, wherein said third mechanism varies said center frequency of said third frequency range from an initial center frequency of approximately 500 Hz.

7. The apparatus according to claim 1, wherein said at least one sensor senses said motion in at least one of six degrees of freedom.

8. The apparatus according to claim 1, wherein said at least one sensor, said sensory converter, and said presentation mechanism are included in a common housing.

9. The apparatus according to claim 1, wherein said presentation mechanism comprises at least one of an earphone, a headphone, a display, and a speaker.

10. The apparatus according to claim 1, wherein said at least one sensor comprises a plurality of sensors to be attached to said user.

11. The apparatus according to claim 1, further comprising:
    a proximity sensor coupled to said sensory converter and configured to detect a relative location of other objects.

12. An apparatus for relieving motion sickness, comprising:
    at least one sensor which senses a motion of an object;
    a sensory converter coupled to said sensor and configured to convert said sensed motion to corresponding sensory signals, said sensory signals having a variation in spectral emphasis in proportion to said sensed motion, comprising:
    a first mechanism configured to vary a frequency of a first signal within a first frequency range in proportion to a sensed pitching motion of said object, said first frequency range having a center frequency of approximately 2000 Hz, and
    a second mechanism configured to vary a frequency of a second signal within a second frequency range in proportion to a sensed yawing motion of said object, said second frequency range having a center frequency of approximately 1000 Hz; and
    a presentation mechanism configured to present said sensory signals to a user.

13. The apparatus according to claim 12, wherein said sensory converter further comprises:
    a third mechanism configured to vary a frequency of a third signal within a third frequency range in proportion to a sensed vertical motion of said object, said third frequency range having a center frequency of approximately 500 Hz.

14. An apparatus for relieving motion sickness, comprising:
    at least one sensor which senses a motion of an object;
    a sensory converter coupled to said sensor and configured to convert said sensed motion to corresponding sensory signals, said sensory signals having a variation in spectral emphasis in proportion to said sensed motion, comprising:
    a first mechanism configured to vary a spectral emphasis of a first frequency range of said sensory signals in proportion to a sensed pitching motion of said object, said first frequency range having a center frequency of approximately 2000 Hz, and
    a second mechanism configured to vary a spectral emphasis of second frequency of said sensory signals in proportion to a sensed yawing motion of said object, said second frequency range having a center frequency of approximately 1000 Hz; and
    a presentation mechanism configured to present said sensory signals to a user.

15. The apparatus according to claim 14, wherein said sensory converter further comprises:
    a third mechanism configured to vary a spectral emphasis of a third frequency range of said sensory signals in proportion to a sensed vertical motion of said object, said third frequency range having a center frequency of approximately 500 Hz.

16. The apparatus according to claim 14, wherein said sensory converter comprises:
    a third mechanism configured to generate at least one of 1) white noise signals, 2) pink noise signals, 3) brown noise signals, 4) popcorn noise signals, and 5) display signals which correspond to said sensory signals.

17. A method for relieving motion sickness, comprising:
    sensing a motion of an object;
    converting said motion sensed in said sensing step to corresponding sensory signals having a variation in spectral emphasis in proportion to said sensed motion, including:

varying, in proportion to a sensed pitching motion of said object, said spectral emphasis of said sensory signals, including varying at least one of 1) a bandwidth and 2) a center frequency of a first frequency range of said sensory signals, and varying, in proportion to a sensed yawing motion of said object, said spectral emphasis of said sensory signals including varying at least one of 1) a bandwidth and 2) a center frequency of a second frequency range of said sensory signals; and presenting said sensory signals to a user.

18. The method according to claim 17, wherein said converting step further comprises:

varying, in proportion to the sensed pitching motion of said object, an amplitude of said first frequency range of said sensory signals; and varying, in proportion to the sensed yawing motion of said object, an amplitude of said second frequency range of said sensory signals.

19. The method according to claim 17, wherein said converting step further comprises:

varying, in proportion to a sensed vertical motion of said object, said spectral emphasis of said sensory signals, including varying at least one of 1) a bandwidth, 2) a center frequency, and 3) an amplitude of a third frequency range of said sensory signals.

20. The method according to claim 17, wherein said sensing step senses said motion in at least one of six degrees of freedom.

21. The method according to claim 17, wherein said presenting step comprises:

using at least one of an earphone, a headphone, a speaker, and a display to present said sensory signals.

22. The method according to claim 17, wherein said converting step further comprises:

generating at least one of 1) white noise signals, 2) pink noise signals, 3) brown noise signals, 4) popcorn noise signals, and 5) display signals which correspond to said sensory signals.

23. The method according to claim 17, wherein said converting step further comprises:

varying, in proportion to said sensed pitching motion of said object, said center frequency of said first frequency range from an initial center frequency of approximately 2000 Hz; and varying, in proportion to said sensed yawing motion, said center frequency of said second frequency range from an initial center frequency of approximately 1000 Hz.

24. The method according to claim 19, wherein said converting step further comprises:

varying, in proportion to said sensed vertical motion of said object, said center frequency of said third frequency range from an initial center frequency of approximately 500 Hz.

25. An apparatus for relieving motion sickness, comprising:

at least one sensor which senses vertical, yawing and pitching motions of an object;

a sensory converter coupled to said sensor and configured to convert the sensed vertical, yawing and pitching motions of the object to corresponding first, second and third audio tone signals having respective first, second and third time intervals between successive audio tone signals which vary in proportion to the respectively sensed vertical, yawing, and pitching motions of the object; and a presentation mechanism configured to present the first, second and third audio tone signals.

26. The apparatus according to claim 25, wherein the sensory converter varies the first, second and third time intervals to decrease in time based on a respectively sensed positive vertical, yawing and pitching motion of the object, and varies the first, second and third time intervals to increase in time based on a respectively sensed negative vertical, yawing and pitching motion of the object.

27. The apparatus according to claim 25, wherein the audio tone signals comprise audio messages.

28. A method for relieving motion sickness, comprising:

sensing vertical, yawing and pitching motions of an object;

converting the sensed vertical, yawing and pitching motions of the object to corresponding first, second and third audio tone signals having respective first, second and third time intervals;

varying the first, second and third time intervals in proportion to the respectively sensed vertical, yawing, and pitching motions of the object; and presenting the first, second and third audio tone signals.

29. The method according to claim 28, wherein the varying step varies the first, second and third time intervals to decrease in time based on a respectively sensed positive vertical, yawing and pitching motion of the object, and varies the first, second and third time intervals to increase in time based on a respectively sensed negative vertical, yawing and pitching motion of the object.

30. The method according to claim 28, wherein the audio tone signals include audio messages.

* * * * *